(12) United States Patent
Woehr

(10) Patent No.: US 8,979,802 B2
(45) Date of Patent: Mar. 17, 2015

(54) SAFETY IV CATHETER ASSEMBLY WITH SEAL

(71) Applicant: B. Braun Melsungen AG, Melsungen (DE)

(72) Inventor: Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 13/975,986

(22) Filed: Aug. 26, 2013

(65) Prior Publication Data

US 2014/0276433 A1  Sep. 18, 2014

Related U.S. Application Data

(60) Provisional application No. 61/788,766, filed on Mar. 15, 2013.

(51) Int. Cl.
*A61M 25/06* (2006.01)
*A61M 25/00* (2006.01)
*A61M 5/32* (2006.01)

(52) U.S. Cl.
CPC ......... *A61M 5/3273* (2013.01); *A61M 25/0618* (2013.01); *A61M 25/0014* (2013.01); *A61M 25/0097* (2013.01); *Y10T 29/49826* (2015.01)

USPC ....................................... 604/164.08; 604/198

(58) Field of Classification Search
CPC ..................... A61M 25/0618; A61M 25/0631; A61M 5/3273; A61M 2005/325
USPC ................................. 604/164.08, 263, 164.12
See application file for complete search history.

(56) References Cited

U.S. PATENT DOCUMENTS

| | | | |
|---|---|---|---|
| 2003/0097098 A1* | 5/2003 | Lavi et al. | 604/263 |
| 2008/0097343 A1* | 4/2008 | Woehr | 604/263 |
| 2008/0097344 A1* | 4/2008 | McKinnon et al. | 604/263 |
| 2008/0108944 A1* | 5/2008 | Woehr et al. | 604/164.08 |
| 2008/0249478 A1* | 10/2008 | Ishikura et al. | 604/198 |
| 2009/0054852 A1* | 2/2009 | Takano et al. | 604/263 |
| 2010/0094216 A1* | 4/2010 | Yue et al. | 604/117 |
| 2011/0272896 A1* | 11/2011 | Kamibayashiyama et al. | 277/650 |

* cited by examiner

*Primary Examiner* — Nicholas Lucchesi
*Assistant Examiner* — Anh Bui
(74) *Attorney, Agent, or Firm* — Klein, O'Neill & Singh, LLP

(57) ABSTRACT

Catheter assemblies are described having a catheter hub with a catheter tube and a needle hub with a needle projecting through the catheter tube. The catheter hub has at least two seals with at least one being a temporary seal that ends or terminates upon movement of a needle and/or a guard. Different needle guards are provided that can be seated differently within the catheter hub to seal against the elastic seal.

21 Claims, 5 Drawing Sheets

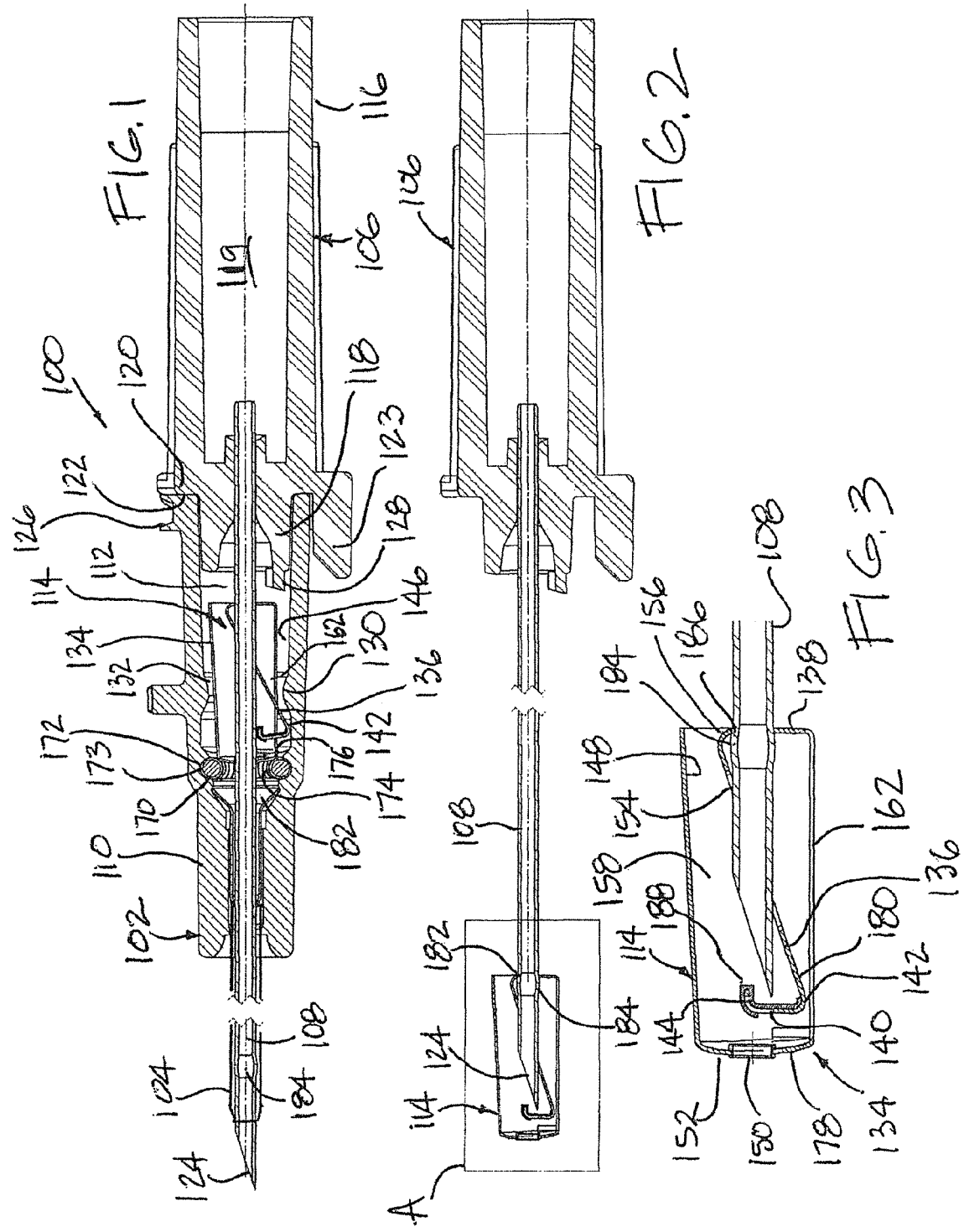

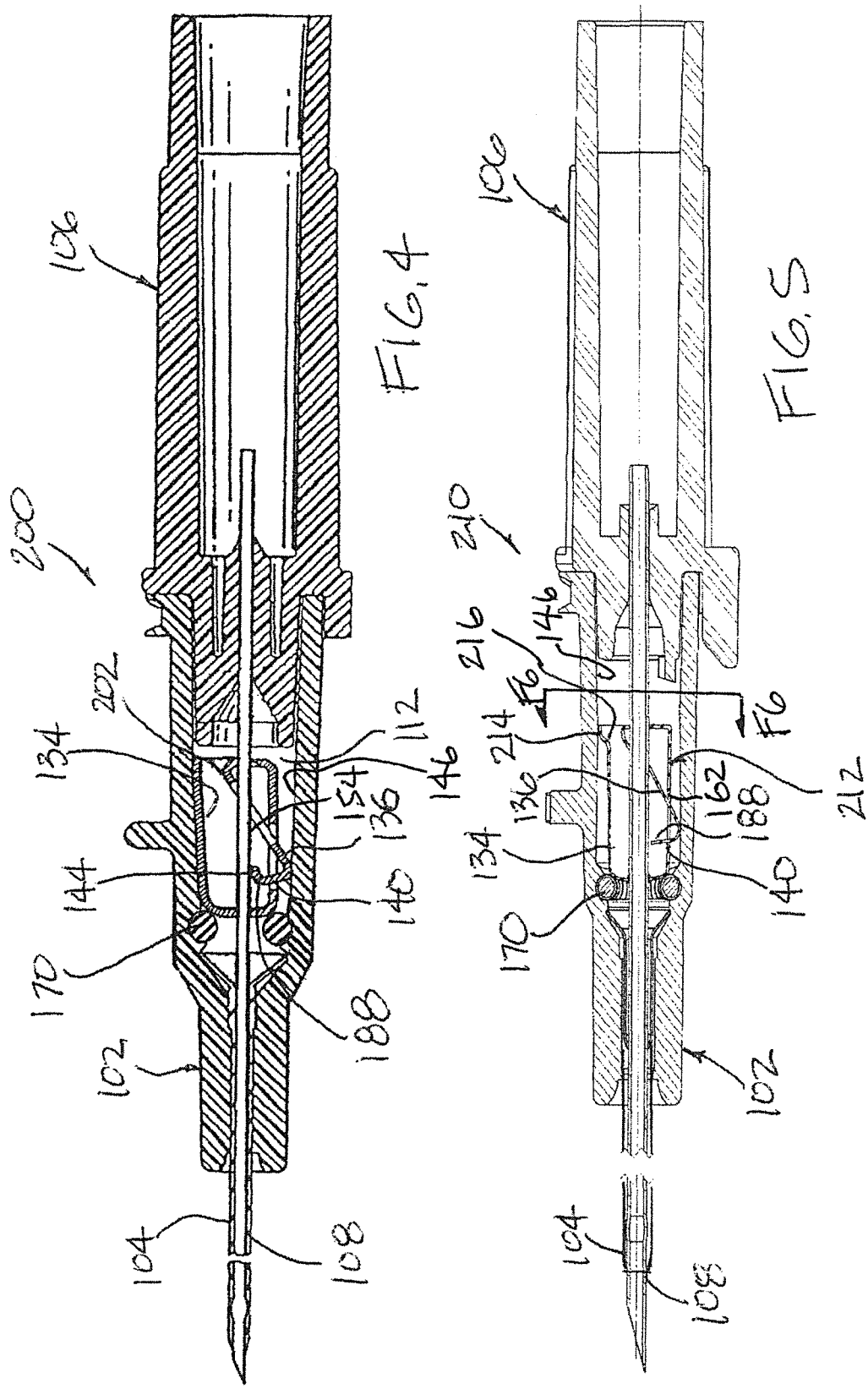

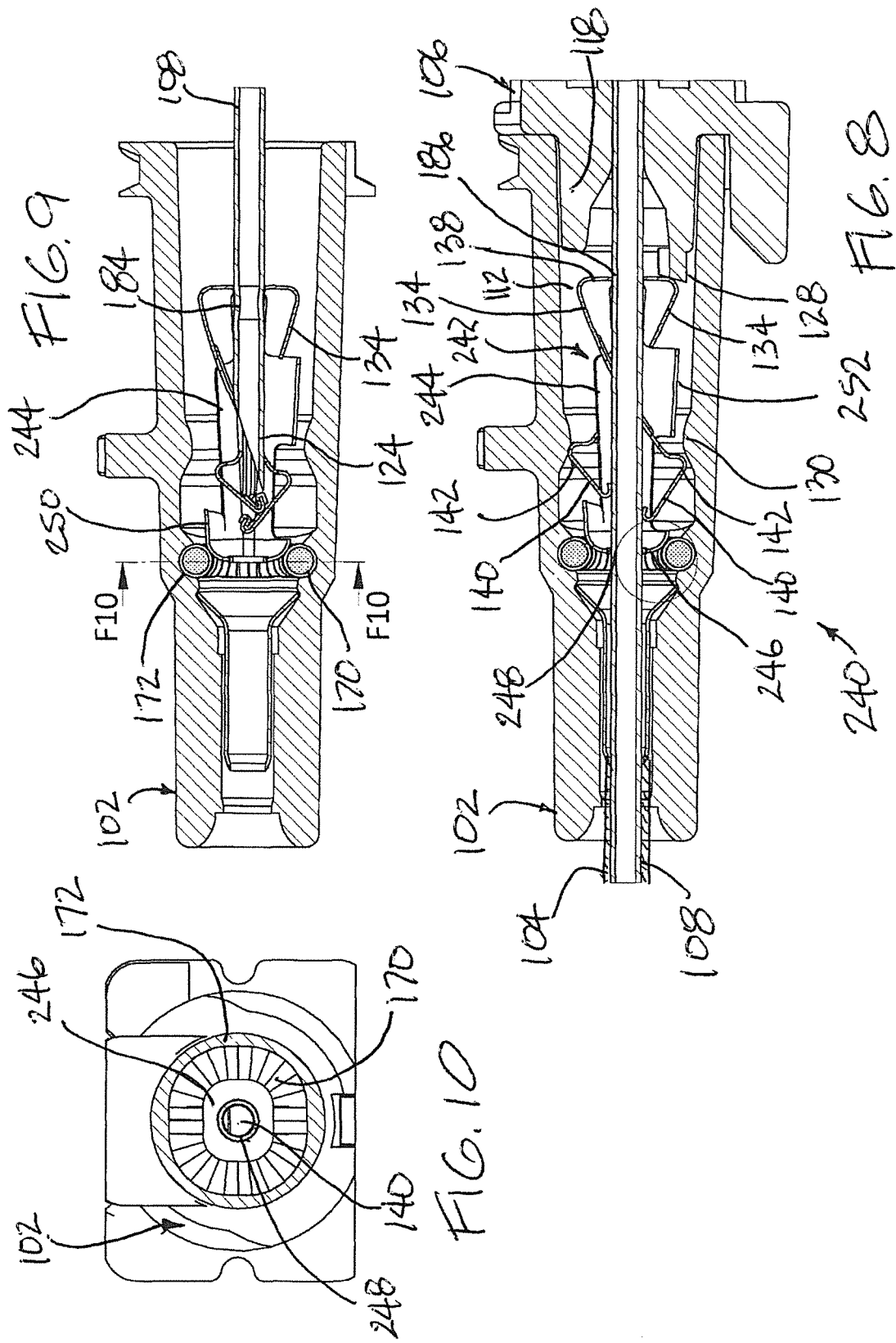

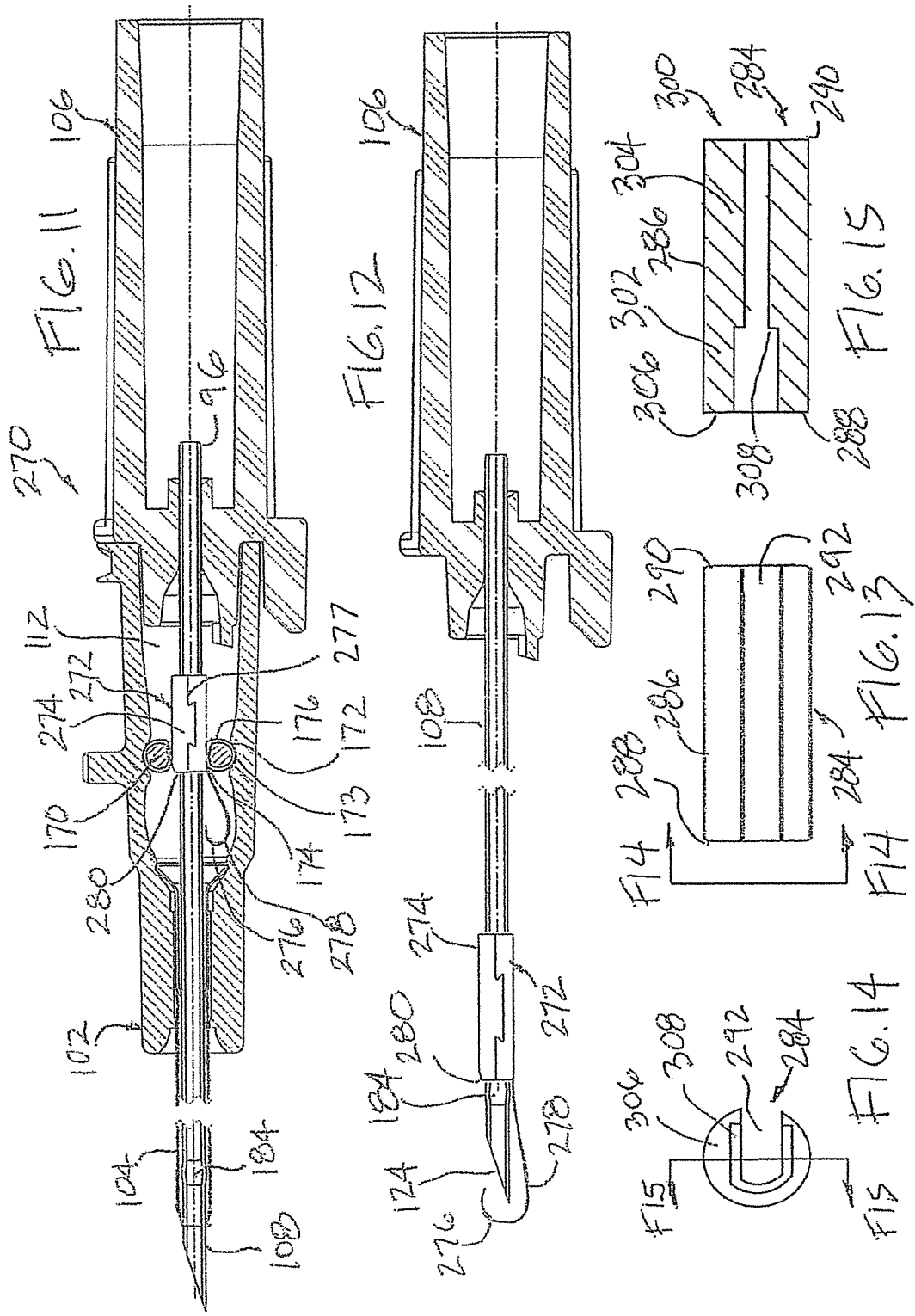

SAFETY IV CATHETER ASSEMBLY WITH SEAL

FIELD OF ART

Catheter assemblies are generally discussed herein for intravenous venipuncture with more specific discussions related to IV catheter assemblies having a tip protector or needle guard and seals for restricting blood flashback.

BACKGROUND

Insertion procedure for an IV catheter (IVC) assembly contains four basic steps: (1) the healthcare worker inserts the needle and catheter together into the patient's vein; (2) after insertion into the vein with the needle point, the catheter is pushed forward into the vein of the patient by the healthcare worker with his or her finger; (3) the healthcare worker withdraws the needle by grasping the catheter hub end while at the same time applying pressure to the patient's vein distal of the catheter to stop the flow of blood through the catheter with his or her free hand; and (4) the healthcare worker then tapes the now inserted catheter to the patient's skin and connects the exposed end of the catheter (the catheter hub) to the source of the fluid to be administered into the patient's vein.

The problem is that immediately after the withdrawal of the needle from the patient's vein, the healthcare worker must place the exposed needle tip at a nearby location and address the tasks required in items (3) and (4) above. It is at this juncture that the exposed needle tip creates a danger of an accidental needle stick, which, under the circumstances, leaves the healthcare worker vulnerable to the transmission of various dangerous blood-borne pathogens, including AIDS and hepatitis from an accidental needle stick.

An additional problem comes if the health care worker inserting the IV catheter stops applying pressure to the vein to use a second hand for step (4) above. This can increase the risk of infection for the patient and causes more work for the health care worker to clean up the blood that may escape from the open catheter hub.

Other needle types similarly expose healthcare workers to risks of accidental needle sticks. For example, a doctor administering an injection, using a straight needle, a Huber needle, a winged infusion needle, etc., may place the used needle on a tray for subsequent disposal by a nurse. For the period between placing the used needle on a tray or a work station to the time it is discarded, the used needle is a potential source for disease transmissions for those that work near or around the needle. Accordingly, all needles should be covered upon withdraw of the needle from the patient to ensure greater worker safety. Ideally, the procedure for covering the needle tip should be passive, self-activating, or at least simple to perform. In addition, the device for covering the needle should be reliable and robust.

SUMMARY

Features of the present disclosure generally relate to an IV catheter assembly having a needle guard for covering the needle tip following successful venipuncture. To facilitate use, the present disclosure further includes an elastic seal for limiting blood flow through the interior cavity of the catheter hub. The needle guard, while described herein for use with a catheter assembly, is also useable with different needle types without an over the needle catheter, such as for blood collection, Seldinger, introducer or for biopsy needles, among others.

An exemplary feature of the present disclosure include a catheter assembly comprising a catheter hub with a catheter tube having a tube end, said catheter hub comprising a body defining an interior cavity comprising a first inside diameter section distal of a second inside diameter section and wherein said first inside diameter section is larger in dimension than said second inside diameter section. The assembly further includes a needle hub with a needle having a needle tip, a nominal needle diameter, and a needle shaft projecting through the catheter hub and the catheter tube such that the needle tip extends distally of the tube end in a ready position. An elastic seal can be held against a shoulder in the interior cavity of the catheter hub, said elastic seal comprising an outside diameter and an inside diameter and wherein said inside diameter being sufficiently larger than the nominal needle diameter so that the needle shaft does not come in contact with the inside diameter of the elastic seal in the ready position. A needle guard for covering the needle tip in a protective position can be located in the interior cavity of the catheter hub and in contact with the elastic seal and wherein a temporary seal for limiting fluid flow is formed at a point where the needle guard contacts the elastic seal.

The catheter assembly wherein the needle guard can comprise a cap comprising a dome surface and wherein the dome surface is axially loaded against the elastic seal. The dome surface can also include a distal wall that contacts the elastic seal.

The catheter assembly wherein a temporary seal can stop or terminate when the needle guard moves in a proximal direction away from the elastic seal, at which point fluid can freely flow through the inside diameter of the elastic seal.

The catheter assembly wherein the elastic seal can be compressed inside a groove located in the interior cavity of the catheter hub and wherein the groove comprises the shoulder.

The catheter assembly wherein the needle guard can comprise a sleeve comprising an inside diameter, an outside diameter, and a length and wherein a change in profile formed near the needle tip has a larger cross-sectional dimension than the inside diameter of the sleeve.

The catheter assembly wherein the needle guard can comprise a surface that contacts the needle shaft and wherein the surface that contacts has a coating applied thereon to reduce friction when the needle shaft moves against the surface.

The catheter assembly can further comprise an installation tool comprising a lengthwise channel for pushing the guard into the interior cavity of the catheter hub.

The catheter assembly wherein the needle guard can further comprise an arm comprising an elbow that contacts the interior surface of the catheter hub.

Another feature of the present disclosure includes a catheter assembly comprising a catheter hub with a catheter tube having a tube end, said catheter hub comprising a body defining an interior cavity having an interior surface with an interior shoulder and a needle hub with a needle having a needle tip, a nominal needle diameter, and a needle shaft projecting through the catheter hub and the catheter tube such that the needle tip extends distally of the tube end in a ready position. An elastic seal is held against the interior shoulder in the interior cavity of the catheter hub, said elastic seal comprising an outside diameter, an inside diameter, and a side surface located between the inside and outside diameters and wherein said inside diameter being sufficiently larger than the nominal needle diameter so that the needle shaft does not come in contact with the inside diameter of the elastic seal in the ready position. A needle guard for covering the needle tip in a protective position is located in the interior cavity of the catheter hub, said needle guard comprising a distal wall having a distal opening and a distally facing surface in contact with the side surface of the elastic seal and wherein a temporary seal for limiting fluid flow is formed at a point where the needle guard contacts the side surface of the elastic seal.

The catheter assembly wherein the interior cavity of the catheter hub can comprise a first inside diameter section distal of a second inside diameter section and wherein the first inside diameter section is larger in dimension than the second inside diameter section.

The catheter assembly wherein the second inside diameter section can include an annular protrusion.

The catheter assembly wherein the first inside diameter section can include an annular groove.

The catheter assembly can further comprise a hydrophobic filter mounted at the distal opening of the distal wall of the needle guard to at least partially cover the distal opening.

The catheter assembly wherein the needle guard can comprise a cap, an arm, a proximal wall, a distal wall, and a curved elbow, and wherein the curved elbow contacts the catheter hub.

The catheter assembly can further comprise micro-channels formed on the elastic seal.

The catheter assembly wherein the needle can further comprise a change in profile located proximally of the needle tip.

A still further feature of the present disclosure is a method for manufacturing a catheter assembly. As disclosed, the method can include the steps of forming a catheter hub with a catheter tube having a tube end, said catheter hub comprising a body defining an interior cavity having an interior surface with an interior shoulder and forming a needle hub with a needle having a needle tip, a nominal needle diameter, and a needle shaft projecting through the catheter hub and the catheter tube such that the needle tip extends distally of the tube end in a ready position. The method can further include placing an elastic seal in the interior cavity of the catheter hub and against the interior shoulder, said elastic seal comprising an outside diameter, an inside diameter, and a side surface located between the inside and outside diameters and wherein said inside diameter being sufficiently larger than the nominal needle diameter so that the needle shaft does not come in contact with the inside diameter of the elastic seal in the ready position and placing a needle guard for covering the needle tip in a protective position in the interior cavity of the catheter hub and in contact with the elastic seal. The method can also include the step of forming a temporary seal for limiting fluid flow through the elastic seal at a point where the needle guard contacts the elastic seal.

The method wherein the needle guard can have a distal wall having a distal opening and a distally facing surface and wherein the distally facing surface contacts the elastic seal.

The method can further comprise pushing the guard into the interior cavity of the catheter hub with an installation tool comprising a lengthwise channel.

The method can further comprise a hydrophobic filter mounted at the distal opening of the needle guard.

The method can further comprise pushing the guard so that an outside surface of the guard is sealed against the inside diameter of the elastic seal.

The method can further comprise adding a coating onto a surface of the needle guard that contacts the needle shaft.

The method wherein the needle guard can exert a force on a distally sloping surface of the interior of the catheter hub to force the needle guard against the elastic seal.

BRIEF DESCRIPTION OF THE DRAWINGS

These and other features and advantages of the present device, system, and method will become appreciated as the same becomes better understood with reference to the specification, claims and appended drawings wherein:

FIG. 1 is a cross-sectional side view of a safety IVC provided in accordance with aspects of the present device, system, and method.

FIG. 2 is a cross-sectional side view of the needle hub of FIG. 1 with the needle tip covered by the needle guard of FIG. 1.

FIG. 3 is an enlarged view of the needle guard of FIG. 2.

FIG. 4 is a cross-sectional side view of an alternative safety IVC provided in accordance with aspects of the present device, system, and method.

FIG. 5 is a cross-sectional side view of another alternative safety IVC provided in accordance with aspects of the present device, system, and method.

FIG. 8 is a cross-sectional side view of yet another alternative safety IVC provided in accordance with aspects of the present device, system, and method.

FIG. 9 is a cross-sectional side view of the safety IVC of FIG. 8 with the needle guard activated to block the needle tip.

FIG. 10 is a cross-sectional end view of FIG. 9 taken along line F10-F10.

FIG. 11 is a cross-sectional side view of still yet another alternative safety IVC provided in accordance with aspects of the present device, system, and method.

FIG. 12 a cross-sectional side view of the safety IVC of FIG. 11 with the needle guard activated to block the needle tip.

FIG. 13 is a side view of an installation tool provided in accordance with aspects of the present device, system, and method.

FIG. 14 is an end view of the installation tool of FIG. 13 taken along line F14-F14.

FIG. 15 is a cross sectional side view of the installation tool of FIG. 14 taken along line F15-F15.

DETAILED DESCRIPTION

Figure 7:
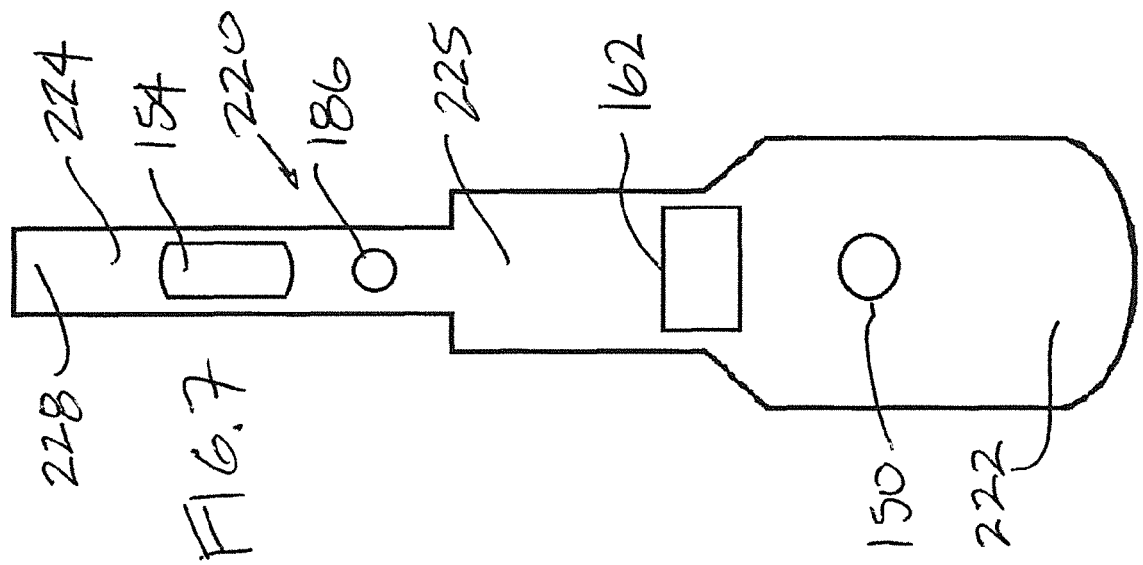
FIG. 7 is a top view of a punched metal sheet usable to form a needle guard.

The detailed description set forth below in connection with the appended drawings is intended as a description of the presently preferred embodiments of safety intravenous catheters or safety IVCs provided in accordance with aspects of the present device, system, and method and is not intended to represent the only forms in which the present device, system, and method may be constructed or utilized. The description sets forth the features and the steps for constructing and using the embodiments of the present device, system, and method in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features. The housing seals and guards can also be used for other needles without an over the needle catheter. For example a sharp stylet of a biopsy needle could have the seals and guards described in the hub of the biopsy needle. Likewise the catheter tubing can be deleted when incorporating friction reducing features with the needle guards to a blood collection or Seldinger or introducer needle devices.

With reference now to FIG. 1, a safety IVC 100 is shown, which comprises a catheter hub 102 with a catheter tube 104 attached thereto and a needle hub 106 having a needle 108 projecting through the catheter hub and the catheter tube in a ready position, which is understood to be ready for use to perform a venipuncture. The catheter hub 102 comprises a hub body 110 defining an interior cavity 112 having a needle guard or tip protector 114 located therein. The needle hub 106 similarly has a hub body 116 defining an interior cavity or flashback chamber 119 having a proximal opening with a female Luer taper. An air permeable vent plug (not shown) may be positioned or attached at the proximal opening of the flashback chamber of the needle hub to stop blood flow from spilling out of the needle hub when the assembly is in use, such as following successful venipuncture.

At the distal end of the needle hub 106, a nose section 118 projects into the proximal female Luer opening of the catheter hub 102 and is stopped by the proximal end surface 120 of the catheter hub abutting a distal shoulder 122 of the needle hub 106. This physical stop allows for proper axial positioning of the needle tip 124 relative to the distal end of the catheter tube 104. In other examples, the nose section 118 may be omitted and the needle tip alignment relative to the catheter tube is still possible by the abutting surfaces 120, 122. Radial alignment between the catheter hub 102 and the needle hub 106 may be accomplished using exterior alignment means, such as the axially extending tab 123 abutting the outer surface of the catheter hub 102. Also shown in FIG. 1 are exterior threads 126 for threaded engagement with a threaded collar, such as a collar of an IV tubing adaptor.

In one example, the nose section 118 has an axially extending tab 128 for pushing the needle guard 114 distally into position in the interior cavity 112 of the catheter hub 102 during assembly. Although not shown, the tab 128 is sized and shaped so as to push the needle guard and remain in abutting contact with the proximal end of the needle guard 114 once the guard is in position, as further discussed below. Alternatively, an installation tool having a lengthwise slot or channel may be used for pushing the guard 114 into position if the extending tab 128 is not incorporated or if not properly sized. As further discussed below, the lengthwise slot on the installation tool allows the tool to be mounted sideways over the needle for pushing the guard into position without having to slip the tool onto the needle from only the needle tip end. Once completed, the same longitudinal slot on the installation tool is used to separate sideways the tool from the needle 108.

In the example shown, the interior cavity 112 of the catheter hub 102 comprises an annular projection 130 forming a reduced interior cross-sectional dimension of the catheter hub. Thus, the interior cavity 112 is understood to comprise a reduced interior section 130 just upstream or distal of a relatively larger interior section 132. Viewed alternatively, the nominal inside diameter distal or upstream of the projection is relatively larger than the reduced diameter section. In other words, the catheter hub has a relatively larger inside diameter upstream of a smaller inside diameter section. In another example, instead of an interior projection 130, an annular groove or recess is provided. Thus, distal of the projection 130 or with the projection omitted, a recess or groove may be provided in the alternative embodiment for retaining the needle guard in the catheter hub. The recess or groove may be viewed as a relatively larger interior section upstream or distal of a relatively smaller interior section, which may be viewed as the nominal inside diameter section. A combination of the groove and projection as shown can also be used.

With reference again to FIG. 1 in addition to FIG. 3, the needle guard 114 comprises a cap 134 and an arm 136, which extends distally of a proximal wall 138. The distal wall 140 is provided at an end of the arm 136 for blocking the needle tip 124 in the protected or protective position shown in FIG. 3. A curved elbow 142 is also provided opposite a curved lip 144.

The cap 134, the arm 136, the proximal wall 138, and the distal wall 140 may be formed as a single or monolithic unit. In another example, the cap 134 may be separately formed from the arm 136, the proximal wall 138 and the distal wall 140. In still another example, the distal wall may be separately formed and attached to the arm. In still yet another example, the distal wall 140 and the arm 136 may be replaced by a different arm extending from the sidewall 148 on the cap, such as forming a cutout on the cap to form a leaf spring to bias the needle. This different arm extending from the sidewall of the cap may operate to tilt or angle the needle tip 124 within the interior space of the cap 134 so that the tip 124 is moved out of alignment and cannot reemerge out the distal opening 150 in the distal wall 152 of the cap 134, which has a dome or dome-like shape having rounded corners. In other example, the distal wall 152 is generally flat and has straight corners. As shown, an arm opening 154 is provided on the arm 136 between the proximal wall 138 and the distal wall 140 for allowing the needle to pass therethrough. In an alternative embodiment, the arm opening 154 is omitted and the arm 136 extends from the upper proximal wall section 156, extends distally but parallel with the needle 108, and the distal wall 140 extends downwardly from the modified arm and contacts the needle shaft with spring bias.

As further discussed below with reference to FIG. 7 and alluded to above, the needle guard 114 may be made from or shaped from a stamped metal sheet, such as a stamped stainless steel metal sheet. The distal wall 152 and the cap sidewall 158 may be formed by subjecting the stamped sheet against a die under relatively high pressure in a coining process. Depending on the edge forming the parting line and the shape of the stamped sheet, different needle guards may be coined. The cap may further include a sidewall opening 162 to allow the curved elbow 142 to project therethrough in the ready position of FIG. 1.

With reference again to FIG. 1, an elastic seal 170 is provided in the interior cavity 112 of the catheter hub. In one example, a recess or groove 172 comprising at least one shoulder is formed in the interior cavity 112 for receiving the elastic seal 170. As shown, two shoulders are provided. The elastic seal 170 is squeezed into the groove 172 and forms a seal against the surface of the groove 172, such as the shoulder, with its outside diameter or outside surface 173. In one example, the elastic seal 170 is an elastomeric O-ring, such as a silicone O-ring or a synthetic rubber O-ring. The seal between the elastic seal 170 and the groove 172 is sufficiently fluid tight to prevent blood from passing thereacross, such as following successful venipuncture where blood can flow into the interior of the catheter hub by way of the annular space between the catheter tube 104 and the needle 108 in what is known as secondary blood flashback.

As shown, the elastic seal 170 has an inside diameter or inside surface 174 and a side surface 176 located between the OD and the ID surfaces 173, 174. The ID 174 is selected, such as being sized and shaped, to provide ample clearance around the needle. For example, the ID 174 of the elastic seal should be selected with a sufficiently large dimension so as not to come in contact with the needle during use. Alternatively the inside surface 174 of the elastic seal 170 can contact and seal against the needle shaft. In one example, the ID may be sized to be about 1.5 times to about 3 or more times larger than the diameter of the needle. In one example, the side surface 176 of the elastic seal 170 is configured to seal against the distal wall surface 178 of the cap 134 of the needle guard 114. For example, when the needle guard 114 is mounted inside the catheter hub and pushed against the elastic seal 170, a seal is formed between the distal wall surface 178 and the elastic seal sidewall surface 176 to prevent or restrict blood flow thereacross. As further discussed below, the seal with the needle guard 114 is therefore a temporary seal that terminates or stops upon proximal movement of the needle guard.

As previously discussed, the axial tab 128 on the nose section 118 of the needle hub is configured to push the needle guard 114, such as the proximal wall 138 of the guard, distally inside the catheter hub to seat the guard against the elastic seal 170. In another example, the guard is pushed distally using an installation tool, as further discussed below with reference to FIGS. 13 and 14. The distal wall 152 of the needle guard 114 should therefore have a cross-sectional dimension greater than the ID 174 of the elastic seal 170 so as to abut against the side surface 176 of the elastic seal, between the ID and the OD. In another example, the distal end of the cap 134 is sufficiently small so as to project into and a section of the cap 134 just proximal of the distal wall 152 of the cap will seal against the ID of the elastic seal 170.

In one example, the curved lip 144 and the curved elbow 142 abuts the needle 108 and the interior surface 146 of the catheter hub 102, respectively, to axially secure the needle guard 114 inside the catheter hub and to push against the elastic seal 170. The curved elbow 142 can project out through the cap 134 via a side opening 162 formed in the body of the cap, as further discussed below with reference to FIG. 6. In an example, the arm surface 180 just proximal of the curved elbow 142 (FIG. 3) is arranged, such as being sized and shaped, to abut against the projection 130 or a groove in the catheter hub to retain the guard inside the catheter hub during retraction of the needle until the needle tip 124 moves proximally of the curved lip 144. The arm surface 180 and/or the projection 130 may also be sized and shaped or positioned so that the arm surface 180 and the projection 130 abut in the ready to use position to maintain an axial load on the guard 114 against the elastic seal 170.

Thus, as shown in FIG. 1, blood flow is sealed or at least restricted from flowing across the gap between the elastic seal 170 and the groove 172 holding the elastic seal 170 and the gap between the elastic seal 170 and the needle guard 114. In one example, micro-channels and/or micro-bumps are provided on the outer surface of the elastic seal 170 so as to permit air to vent thereacross between the elastic seal and the groove 172 but not large enough for blood to freely flow therebetween. Alternatively or in addition thereto, a seal (not shown), such as a hydrophobic filter, is placed at the opening 150 of the cap 134 of the needle guard 114 to permit venting but not blood flow. For example, a sheet of hydrophobic filter may be glued to the cap 134 at the opening 150 of the cap and the needle 108 is then allowed to penetrate therethrough during assembly. Following successful venipuncture, air can vent through the hydrophobic filter but not blood to enable secondary blood flashback. During withdraw of the needle from the catheter hub following use, the hole in the hydrophobic filter formed by the needle can also function as a wiper to wipe blood from the exterior surface of the needle. The hydrophobic filter therefore allows air to vent to permit blood flashback while also performs a wiping function to wipe blood from the exterior surface of the needle as the needle is retracted during removal of the needle following successful venipuncture. Exemplary hydrophobic filters include those made from spun bound PP, PTFE fibers, or PCTE (polycarbonate track etch membranes), which have pores that are small enough to permit air to vent thereacross but not blood.

As described, the present device, system, and method are understood to include a catheter assembly comprising a catheter tube attached to a catheter hub, which comprises a body defining an interior cavity. A needle comprising a needle tip is attached to a needle hub and projects through the catheter hub and the catheter tube in a ready position. An elastic seal and a needle guard are positioned in the interior cavity of the catheter hub. The needle guard may be seated inside the catheter hub so that it touches, abuts, or is otherwise squeezed by the elastic seal in a ready position to form a temporary seal with the elastic seal that ends or terminates upon proximal movement of the needle guard. Thus, the present assembly is understood to include a seal between a catheter hub and an elastic seal and between the elastic seal and a needle guard. In another example, a seal is provided at a distal guard opening to form a third seal with the needle inside the catheter hub. Like the seal with the needle guard, the third seal is also a temporary seal that ends or terminates upon the needle moving proximally of the third seal. In some examples, the seal between the elastic seal and the catheter hub can also be a temporary seal and can allow fluid to leak thereacross when a load or pressure is released or removed from the elastic seal. The assembly can therefore be understood to include a safety IVC with one permanent seal and two temporary seals that terminate. If the elastic seal is sealed to the catheter hub only by external load, then the assembly can be understood to include three temporary seals.

During catheterization, blood will flashback into the cavity 119 of the needle hub 106 but is stopped from spilling out of the hub 106 by a vent plug (not shown). Similarly, blood will flashback into the distal cavity chamber 182 of the catheter hub 102, distal of the elastic seal 170, but not freely flow or flow at all into the proximal chamber of the catheter hub 102 until the needle guard is unseated from its ready position, such as until the needle guard backs away from the elastic seal 170. In one example, the temporary seal may be terminated by first retracting the needle hub 106 and the needle 108 from the catheter hub 102 and catheter tube 104, such as by holding onto the catheter hub while retracting the needle hub in a proximal direction. As the needle 108 is retracted, a bump, crimp, or sleeve 184, broadly referred to as a change in profile, moves against the distal side of the proximal wall 138 of the needle guard and is stopped by a perimeter defining an opening 186 on the proximal wall. The change in profile 184 has a larger cross-sectional dimension than the opening 186 on the proximal wall 138 and therefore, from the perspective of the change in profile 184, pushes the needle guard 114 at the proximal wall in the proximal direction. As the needle guard 114 moves in the proximal direction, it is unseated from the ready position and the seal between the guard 114 and the elastic seal 170 terminates, ends or otherwise ceases. In other examples, the change in profile is omitted and the needle guard is equipped with at least two openings having the needle passing therebetween. In the protective position, the guard deflects so that the two openings cant over to grip the outer surface of the needle without the change in profile.

As shown in FIG. 1 the curved elbow 142 is slightly distal of the projection 130. It is to be understood that if the curved elbow engages the distally sloping side of projection 130 then there will be a constant distally directed force pushing the needle guard into contact with the elastic seal 170. When this is the case, then the contact with axially extending tab 128 is not needed and axially extending tab 128 can be deleted.

FIG. 2 is a cross-sectional side view of the needle hub 106, the needle 108, and the needle guard 114 of FIG. 1 after being removed from the catheter hub 102 following successful venipuncture. As shown, the arm 136 on the guard 114 moves in a radial direction to move the distal wall 140 distal of the needle tip 124 to block the needle tip. In an alternative embodiment, the change in profile 184 is omitted and a tether is instead used and is connected at its two ends to the needle hub and the guard. The tether is configured to pull on the needle guard, by way of the needle hub 106 moving in the proximal direction, to remove the guard from the catheter hub. The tether, if used, would also prevent the guard from falling distally off of the needle. In other words the tether prevents the needle tip from pulling through the needle guard.

During removal of the needle 108 from the catheter hub 102, such as in moving the needle from the position shown in FIG. 1 to that shown in FIG. 2, the needle shaft is dragged across the curved lip 144 on the needle guard 114 while the needle guard is held relatively stationary until the needle tip moves proximally of the curved lip 144. Depending on the design of the curved lip 144, a relatively large drag can be felt by the user. The friction may also cause the guard 114 to move slightly proximally until the arm surface 180 adjacent the curved elbow 142 of the needle guard 114 contacts the projection 130 in the catheter hub. While friction between the needle shaft and the curved lip 144 is minimal compared to if the distal wall 140 is left with a blunt end to contact against the side of the needle shaft, in one example, a friction reducing mechanism is provided to further reduce friction between the needle and the needle guard. As shown in FIG. 3, which is an enlarged view of FIG. 2 taken at A, a coating 188 is provided over at least part of the distal wall 140 and the curved lip 144. The coating 188, which is made from a different material than the distal wall 140 and the curved lip 144, may be applied to the stamped metal sheet prior to folding or shaping the sheet into the guard or can be applied after the shaping step to form the guard. In one example, the coating 188 is made from a polyethylene (PE) material. In another example, the coating 188 is made from TEFLON. The coating 188 reduces the coefficient of friction of the guard 114, which allows the guard to optionally be formed without the curved lip 144, i.e., leaving the distal wall 140 with a blunt end. The guard 114 with coating 188 to reduce the guard's coefficient of friction represents a further aspect of the present device, system, and method apart from the catheter assembly and apart from the catheter assembly with an elastic seal 170. In other words, where the guard 114 contacts the needle 108 and where friction can be felt during proximal movement to separate it from the catheter hub, a coating 188 may be applied to reduce the coefficient of friction and therefore the drag experienced by the needle as it moves across the stationary surfaces of the needle guard.

Thus, an aspect of the present device, system, and method is further understood to include a needle guard 114 having a coating 188 to reduce the guard's coefficient of friction. In a further aspect of the present device, system, and method, the guard 114 comprises a cap 134 comprising a distal wall 152 having an opening 150. The guard can also include an arm extending 136 distally of a proximal wall 138 and having a distal wall 140 having the coating 188 located at least in part thereon. In a further aspect of the present device, system, and method, the guard with the coating may be used with a catheter assembly in a safety IVC application. The catheter assembly may further include an elastic seal and the guard may further include a cap for abutting against the elastic seal, such as that shown in FIG. 1.

With reference now to FIG. 4, an alternative catheter assembly is shown 200, which is similar to the catheter assembly 100 of FIG. 1 with a few exceptions. Thus, the catheter assembly 200 comprises a needle hub 106 with a needle 108 and a catheter hub 102 with a catheter tube 104. The catheter hub further comprises a cavity 112 comprising an elastic seal 170 and a needle guard 202. As shown, the needle guard 202 comprises a cap 134 and an arm 136 comprising a distal wall 140. In the present embodiment, the guard 202 is seated in the interior cavity 112 of the catheter hub by both biasing the distal end of the arm 136 against the needle 108 and the interior surface of the catheter hub 102 as well as contacting part of a lengthwise section of the cap 134 against the interior surface of the catheter hub. This allows the guard 202 to be seated and abutted against the elastic seal 170 by action of both the arm 136 and the cap 134. In a preferred embodiment, a coating 188 is applied, at least in part, to the distal wall 140 to reduce the coefficient of friction between the needle 108 and the distal end of the arm 136, such as the curved lip 144 against the needle 108. In an alternative embodiment, the curved lip 144 is omitted and the distal end of the distal wall 140, i.e., a blunt end, coated with the coating 188 contacts the side of the needle.

With reference now to FIG. 5, another alternative catheter assembly is shown 210, which is similar to the catheter assembly 100 of FIG. 1 with a few exceptions. Thus, the catheter assembly 210 comprises a needle hub 106 with a needle 108 and a catheter hub 102 with a catheter tube 104 and interior surface 146. A projection or groove is not shown but could be present and functions as described above. The catheter hub 102 further comprises a cavity 112 comprising an elastic seal 170 and a needle guard 212. As shown, the needle guard 212 comprises a cap 134 and an arm 136 comprising a distal wall 140. In the present embodiment, the guard 212 is seated in the interior cavity 112 by both biasing the distal end of the arm 136 against the needle 108 and the interior surface of the catheter hub as well as contacting a raised section 214 of the cap 134, i.e., a portion of the cap 134, against the interior surface of the catheter hub. This allows the guard 212 to be seated and abutted against the interior surface 146 of the catheter hub 102 at two points provided by the cap and the arm. As only a relatively small section of the cap 134 contacts the interior surface of the catheter hub 102 compared to the embodiment of FIG. 4 which has a large lengthwise section of the cap contact the catheter hub, less force is required to remove the guard 212 from the catheter hub 102. In a preferred embodiment, a coating 188 is applied, at least in part, to the distal wall 140 of the arm to reduce the coefficient of friction between the needle 108 and the distal end of the arm 136, such as between the curved lip 144 and the needle. In an alternative embodiment, the curved lip 144 is omitted and the distal end of the distal wall 140, i.e., a blunt end, coated with the coating 188 contacts the side of the needle. The coating 188 can be sufficiently soft and thick so as to capture the tip of the needle in the protected position (e.g., FIGS. 2 and 3) so that the needle tip cannot slide along the inside surface of the distal wall 140. If a soft coating is used that can capture the needle tip, the lip 144 at an end of the distal wall 140 may be omitted.

Figure 6:
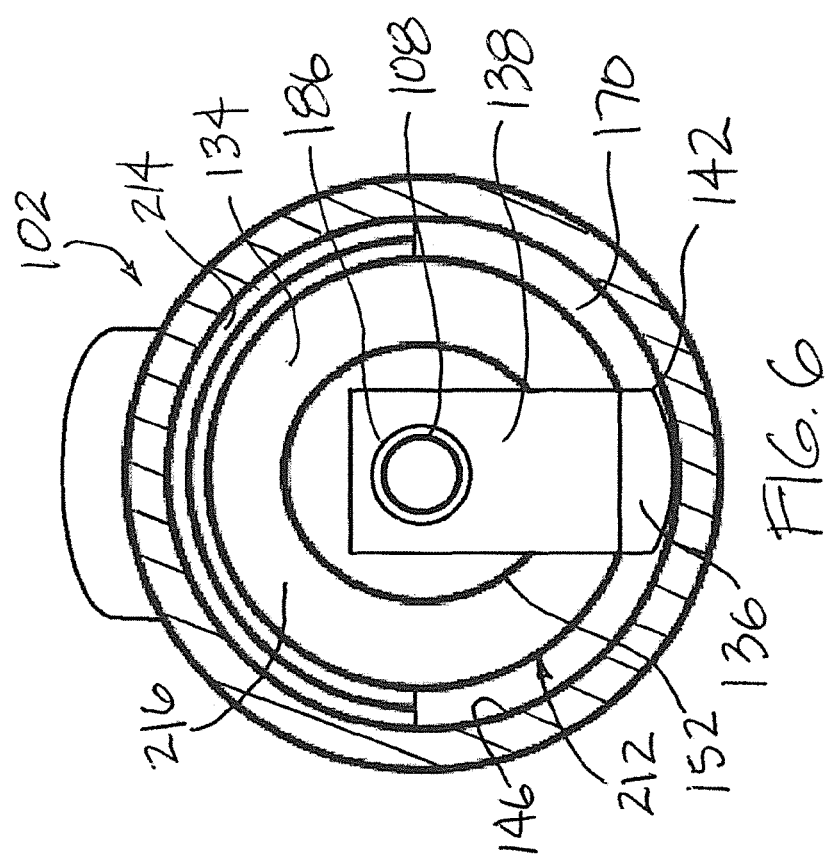
FIG. 6 is an end view of FIG. 5 taken along line F6-F6.

FIG. 6 is an end view of the catheter assembly of FIG. 5 taken along line F6-F6. As shown, the raised section 214 extends radially outwardly of the main cap body 134 to contact the interior surface 146 of the catheter hub 102. The curved elbow 142 similarly extends radially outwardly to contact the interior surface 146 of the catheter hub 102. As shown, there is no protrusion or groove in or on the interior surface 146 of the catheter hub for clarity. The two contact points with the catheter hub 102 are configured to seat the needle guard 212 within the interior cavity of the catheter and in axial contact with the elastic seal 170. As also explained above, if the curved elbow 142 were to engage a distally sloping portion of a groove or projection 130, then there would be a constant distally directed force of the needle guard against the elastic seal 170. Also shown in FIG. 6 is the proximal wall 138 with the needle 108 disposed in the proximal opening 186.

FIG. 7 is a top view of a stamped metal sheet 220 provided in accordance with aspects of the present device, system, and method. The sheet 220 comprises a large section or first section 222 and a relatively narrower section or second section 224. The first section 222 has a first stamped cutout 150 and a relatively larger second stamped cutout 162. When coined with a die, the first cutout 150 and the surface adjacent thereto form the distal opening 150 and the distal wall 152 of the cap 134 of FIGS. 1-5. The first section 222 may be altered and/or the die altered to yield an appropriately sized and shaped cap configuration for the intended application. Opening 162 allows the curved elbow 142 to project outwardly to contact the interior surface of the catheter hub 146 (See, e.g., FIG. 1).

The second section 224 of the stamped metal sheet 220 is configured to form the arm 136 and the distal wall 140 of the guard of FIGS. 1-5. The second section 224 has a first cutout 186 and a second cutout 154. When folded, the first cutout 186 and the surface adjacent thereto form the proximal wall 138 and the proximal opening 186 on the needle guard. The second cutout 154 on the stamped sheet forms an opening (FIG. 3) on the arm 136 of the needle guard when folded, which allows the needle to project therethrough. The end portion 228 of the second section 224 forms the distal wall 140, the curved elbow 142, and optionally the curved lip 144, which may be omitted when incorporating a coating 188. The stamped metal sheet 220 also comprises a middle width section 225. The middle width section 225 is wider to contain the opening 162, which must be wider than the second section 224 so that the curved elbow formed from second section 224 can pass therethrough. Optionally the portion of the second section 224 can be punched even narrower than the rest of second section 224 so that the opening 162 and the middle section 225 can be made relatively narrower.

FIG. 8 is a cross-sectional side view of another alternative catheter assembly 240 provided in accordance with aspects of the present device, system, and method, which is similar to the catheter assembly 100 of FIG. 1 with a few exceptions. Thus, the catheter assembly 240 comprises a needle hub 106 with a needle 108 and a catheter hub 102 with a catheter tube 104. The catheter hub further comprises a cavity 112 comprising an elastic seal 170 located within an interior groove 172 and a needle guard 242. As shown, the needle guard 242 comprises a cap 244 and two arms 136 each comprising a distal wall 140. The guard 242 of FIG. 8 is similar to the guard of FIGS. 4-12 of US Publication No. 2012/0046620 A1, published Feb. 23, 2012, U.S. Ser. No. 13/257,572. As discussed in the '572 application, the cap 244 may be separately formed and subsequently attached to the two arms 136, which are formed with the proximal wall 138 having an opening 186 sized to stop a change in profile 184 on the needle 108. Curved lips 144 are shown at the ends of the two distal walls, which may each include a coating 188 to lower the coefficient of friction between the guard and the needle.

The cap has a distal dome section 246 with a distal wall comprising a distal opening 248 and a dome extension 250 (FIG. 9), which extends in the proximal direction so as to partially cover the distal end of the cap cavity. The cap 244 further includes two stays 252 (only one shown) on either side of the needle.

In one embodiment, the two elbows 142 on the two arms 136 are seated against the distally sloping surface of annular projection 130, and/or alternatively in an annular groove, so as to force the guard forward so that the dome 246 abuts the elastic seal 170 to temporarily seal there-against. In the ready position shown in FIG. 8, a first seal is provided between the elastic seal 170 and the annular groove 172 of the catheter hub and a second seal is provided between the elastic seal 170 and the dome 246, which is a temporary seal that can end upon retraction of the needle guard in the proximal direction. Furthermore, if a hydrophobic filter is provided at the distal opening 248 of the dome 246, a third temporary seal is provided to restrict, limit, or stop blood from flowing proximally past the filter to freely flow into the cavity section 112 of the catheter hub and into the needle guard 242. This third temporary seal may end or terminate upon removal of the needle form the hydrophobic filter.

As shown, the axial tab 128 on the nose section 118 of the needle hub 106 pushes on the proximal wall 138 and remains in contact with the proximal wall. This configuration allows for the assembly of the guard in the catheter hub 102 by simply pushing the needle hub 106 forward to push the proximal wall 138 of the needle guard 242 forward. During the distal travel to seat the needle guard 242, the two elbows 142 and the two arms 136 will flex inwardly when they contact the annular protrusion or projection 130 inside the catheter hub and will rebound slightly after moving distal of the smallest diameter section at the peak of the projection 130. Concurrently therewith, the dome 246 will make contact with the elastic seal 170 and will remain axially loaded against the elastic seal due to the contacts at the two elbows 142 with the projection 130. In an alternative embodiment, a gap is provided between the nose section 118 and the proximal wall 138 in the ready position. If the gap is provided, then the guard 242 can instead be seated using an installation tool, as further discussed below, instead of being pushed by the axial tab 128 at the nose section.

As described, the present device, system, and method include a catheter assembly comprising a catheter tube attached to a catheter hub, which comprises a body defining an interior cavity. A needle comprising a needle tip is attached to a needle hub and projects through the catheter hub and the catheter tube in a ready position. An elastic seal and a needle guard are positioned in the interior cavity of the catheter hub. The needle guard may be seated inside the catheter so that it touches, abuts, or is otherwise pushed distally forward against the elastic seal. In one example, two arms are provided and are biased against an annular projection and/or an annular groove formed in the interior cavity of the catheter hub to maintain an axial load on the elastic seal. Contacts between the two arms and the annular protrusion allows for the distally directed axial force to be imparted on the guard against the elastic seal. Thus, a first seal is provided between the catheter hub and the elastic seal and a second temporary seal is provided between the elastic seal and the needle guard, which can terminate or end upon removal of the guard in the proximal direction. In another example, a seal is provided at a distal guard opening to form a third temporary seal in the catheter assembly. Thus, the catheter assembly is understood to have a seal for restricting or limiting flow formed by contacting a cap section of the needle guard against an elastic seal. Said seal being a temporary seal that ends or terminates upon movement of a catheter component, such as the needle and/or the guard.

FIG. 9 is a cross-section side view of the catheter assembly 240 of FIG. 8 after the needle 108 is retracted and the needle tip 124 moves proximally of both distal walls 140. As shown, the two arms are no longer biased against the side of the needle and flex radially inwardly. The distal walls 140 also move in a radial direction in front of the needle tip to block the needle tip. During this procedure, the dome section 246 of the cap 244 remains in contact with the elastic seal 170 to maintain the seal until further proximal movement of the needle from the point or position shown in FIG. 9. At that moment, further proximal movement of the needle will cause the change in profile 184 to push, or from the perspective of the needle hub to pull, against the perimeter of the proximal opening 186 to move the needle guard 242 proximally out of the catheter hub. Thus, a seal is provided between the catheter hub and the elastic seal and another seal is provided between the elastic seal and the needle guard that can end or terminate. In the present embodiment, the temporary seal remains intact even during initial needle travel in the proximal direction following successful venipuncture. In a particular example, the seal between the guard and the elastic seal comprises a seal between the cap on the guard and the elastic seal. Said temporary seal is only terminated or broken upon the change in profile on the needle contacting a perimeter defining an opening and moving the perimeter and/or the proximal wall, and hence the needle guard, away from the elastic seal.

FIG. 10 is a cross-section end view of FIG. 9 taken at line F10-F10. The present end view clearly shows the annular groove 172, the elastic seal 170, the dome section 246 of the needle guard 242, the opening 248 on the dome section optionally with a hydrophobic filter, and part of the distal walls 140 of at the end the arms 136.

With reference now to FIG. 11, a cross-sectional side view of another alternative catheter assembly 270 provided in accordance with aspects of the present device, system, and method is shown, which is similar to the catheter assembly 100 of FIG. 1 with a few exceptions. Thus, the catheter assembly 270 comprises a needle hub 106 having a needle 108 and a catheter hub 102 having a catheter tube 104. The catheter hub further comprises a cavity 112 comprising an elastic seal 170 located within an interior groove 172 and a needle guard 272. As shown, the needle guard 272 comprises a sleeve 274 and an arm 278 extending distally thereof. The guard 272 may be made from a stamped metal sheet, similar to the stamped sheet of FIG. 7. For example, the first stamped section 222 may be rolled to form the sleeve 274 and the second stamped section 224 folded to form the arm 278 extending distally of the sleeve. Thus, the sleeve has a parting line 277 defined by the two edges of the first stamped section 222. The arm 278 is shown with a continuous curved distal end 276 as opposed to a distinct elbow, distal wall and curved lip, similar to the guard of FIG. 1. In an alternative embodiment, the arm may be folded with a distinct curved elbow, distal wall, and curved lip, similar to the guard of FIG. 1. A coating 188 may be applied to the curved distal end 276 to reduce the coefficient of friction between the guard and the needle.

In an example, the sleeve 274 is formed with a length, an outside diameter, and an inside diameter. Preferably, the inside diameter of the sleeve 274 is sufficiently larger than the outside diameter of the needle 108 but smaller than the largest cross-sectional dimension of the change in profile 184. This allows the needle 108 to freely move relative to the sleeve 274 but not the change in profile 184, which is larger than the inside diameter of the sleeve and therefore will abut and be stopped by the distal end 280 of the sleeve. Thus, when the needle 108 is retracted from the catheter hub 102, such as following successful venipuncture, the change in profile 184 will abut or hit the distal end 280 of the sleeve and will, from the perspective of the change in profile, push on the sleeve 274 to separate it from the elastic seal 170, as further discussed below.

The elastic seal 170 comprises an outside diameter 173, an inside diameter 174, and a side portion 176 located therebetween. As shown, the outside diameter of the sleeve 274 projects through the elastic seal 170 so that the inside diameter 173 of the elastic seal compresses and seals against the outside surface of the sleeve 274. Thus, a seal is provided between the groove 172 and the elastic seal 170 and between the elastic seal 170 and the sleeve 274. To limit or restrict blood flow in the annular space between the needle 108 and the sleeve 274, medically safe lubricant or other benign inserts may be used to seal the annular space.

The needle guard 272 may be installed inside the catheter hub 102 by first mounting the needle guard including the sleeve 274 onto the needle 108 by way of the butt-end 96 of the needle. If the change in profile 184 has not been formed or created until after the guard is mounted onto the needle, then the needle guard may be mounted over the needle via the needle tip end. The elastic seal 170 is then placed over the sleeve 274 as shown in FIG. 11. The combination elastic seal 170 and guard 272 can then be pushed distally into position using an installation tool, which is further discussed below with reference to FIGS. 13 and 14. Alternatively the same shape of the insertion tool can be formed on the nose section 118 and the nose section 118 can push the elastic seal and needle guard into the catheter hub. Once the combination reaches the recess 172 with a shoulder in the interior cavity, a slightly higher resistance follow by a drop in resistance will indicate that the elastic seal 170 has firmly seated within the groove.

FIG. 12 is a cross-sectional side view of the needle hub 106 and needle 108 removed from the catheter hub of FIG. 11 with the needle guard 272 activated at the needle tip 124 to cover the needle tip from accidental needle sticks. The engagement between the change in profile 184 and the distal and 280 of the sleeve 274 prevents the sleeve from traveling further distally off of the needle. The curved distal end portion 276 blocks the needle tip 124 and prevents accidental contact therewith.

FIG. 13 is a side view of an installation tool 284 provided in accordance with aspects of the present disclosure. The installation tool comprises an elongated body portion 286 having an outside diameter and an inside diameter. In some examples, the first end 288 and the second end 290 may have the same inside and outside dimensions. In other examples, the first end 288 and the second end 290 have different inside and outside dimensions. The length of the body section 286 and the dimensions of the first end 288 and the second end 290 may be adjusted or modified based on the particular needle guard or tip protector to be pushed or installed within the catheter hub. For example, the length may be selected to ensure proper reach in order to adequately push the guard and/or elastic seal inside the catheter hub and long enough to be gripped or manipulated from outside the hub. The tool 284 shown may be used to push one of the needle guards disclosed elsewhere herein forward and into the catheter hub to seat the guard against the elastic seal 170. The tool 284 may also be used for any catheter assembly where the axial tab 128 on the nose section 118 of the needle hub 106 is either not incorporated or is too short to adequately push the needle guard forward into the ready position. A lengthwise channel 292 is provided on the body 286 to facilitate mounting the tool 284 over the needle 108 without having to slip the tool 284 onto the needle only at the needle tip 124 or the butt-end 96.

FIG. 14 is an end view of the tool 284 of FIG. 13 taken along line F14-F14. In one embodiment, the tool 284 is molded from a plastic material to include an internal stepped feature. In another example, the tool is made from two parts, which include an outer cylinder with a channel and a separate stepped feature.

FIG. 15 is a cross-sectional side view of the tool 284 of FIG. 14 taken along line F15-F15. The tool has an insert 300 comprising stepped features 302, 304 for use with the guard 272 of FIG. 11. In other examples, different shaped inserts may be used. The insert 300 may form part of the body 286 or be separately formed and attached to the outer shell 286. As shown, the stepped feature comprises a lengthwise step 302 and a rear plate 304. The lengthwise step 302 has a first pusher surface 306 and the rear plate 304 has a second pusher surface 308. The length and other dimensions of the insert 300 are selected so that the insert seats over the sleeve 274 of the guard of FIG. 11 and the first pusher surface 306 contacts the elastic seal 170 while the second pusher surface 308 contacts the proximal end of the sleeve 274. As the tool 284 with the insert 300 is pushed forward, the two pusher surfaces 306, 308 simultaneously push the combination elastic seal 170 and guard 272 in place inside the catheter hub 102.

Although limited embodiments of safety IVCs and other needles described herein and their components have been specifically described and illustrated herein, many modifications and variations will be apparent to those skilled in the art. For example, the various catheter assemblies may incorporate antimicrobial features into the elastic seals and the guards may be made from multiple components and/or include additional or other features. Furthermore, it is understood and contemplated that features specifically discussed for one catheter embodiment may be adopted for inclusion with another catheter embodiment, provided the functions are compatible. For example, the installation tool discussed with reference to FIGS. 11 and 12 may be used to install the guard of FIG. 1, with some modifications to the tool to fit the features of the guard. Accordingly, it is to be understood that the safety IVCs and their components constructed according to principles of the disclosed device, system, and method may be embodied other than as specifically described herein. The disclosure is also defined in the following claims.

What is claimed is:

1. A catheter assembly comprising:
   a catheter hub with a catheter tube having a tube end, said catheter hub comprising a body comprising an interior surface defining an interior cavity comprising a first inside diameter section distal of a second inside diameter section and wherein said first inside diameter section is larger in dimension than said second inside diameter section;
   a needle hub with a needle having a needle tip, a nominal needle diameter, and a needle shaft projecting through the catheter hub and the catheter tube such that the needle tip extends distally of the tube end in a ready position;
   an elastic seal held against a shoulder in the interior cavity of the catheter hub, said elastic seal comprising an outside diameter and an inside diameter and wherein said inside diameter being sufficiently larger than the nominal needle diameter so that the needle shaft does not come in contact with the inside diameter of the elastic seal in the ready position;
   a needle guard for covering the needle tip in a protective position located in the interior cavity of the catheter hub and in contact with the elastic seal;
   a temporary seal for limiting fluid flow formed at a point where the needle guard contacts the elastic seal.

2. The catheter assembly of claim 1, wherein the needle guard comprises a cap comprising a dome surface and wherein the dome surface is axially loaded against the elastic seal.

3. The catheter assembly of claim 1, wherein the temporary seal terminates when the needle guard moves in a proximal direction at which point fluid can freely flow through the inside diameter of the elastic seal.

4. The catheter assembly of claim 1, wherein the elastic seal is compressed inside a groove comprising the shoulder.

5. The catheter assembly of claim 1, wherein the needle guard comprises a sleeve comprising an inside diameter, an outside diameter, and a length and wherein a change in profile formed near the needle tip has a larger cross-sectional dimension than the inside diameter of the sleeve.

6. The catheter assembly of claim 1, wherein the needle guard comprises a surface that contacts the needle shaft and wherein the surface that contacts has a coating applied thereon to reduce friction when the needle shaft moves against the surface.

7. The catheter assembly of claim 1, further comprising an installation tool comprising a lengthwise channel for pushing the guard into the interior cavity of the catheter hub.

8. The catheter assembly of claim 1, wherein the needle guard comprises an arm comprising an elbow that contacts the interior surface of the catheter hub.

9. A catheter assembly comprising:
   a catheter hub with a catheter tube having a tube end, said catheter hub comprising a body defining an interior cavity having an interior surface with an interior shoulder;
   a needle hub with a needle having a needle tip, a nominal needle diameter, and a needle shaft projecting through the catheter hub and the catheter tube such that the needle tip extends distally of the tube end in a ready position;
   an elastic seal held against the interior shoulder in the interior cavity of the catheter hub, said elastic seal comprising an outside diameter, an inside diameter, and a side surface located between the inside and outside diameters and wherein said inside diameter being sufficiently larger than the nominal needle diameter so that the needle shaft does not come in contact with the inside diameter of the elastic seal in the ready position;
   a needle guard for covering the needle tip in a protective position located in the interior cavity of the catheter hub, said needle guard comprising a distal wall having a distal opening and a distally facing surface in contact with the side surface of the elastic seal;
   a temporary seal for limiting fluid flow formed at a point where the needle guard contacts the side surface of the elastic seal.

10. The catheter assembly of claim 9, wherein the interior cavity of the catheter hub comprises a first inside diameter section distal of a second inside diameter section and wherein the first inside diameter section is larger in dimension than the second inside diameter section.

11. The catheter assembly of claim 10, wherein the second inside diameter section is an annular protrusion.

12. The catheter assembly of claim 9, further comprising a hydrophobic filter mounted at the distal opening of the distal wall of the needle guard to at least partially cover the distal opening.

13. The catheter assembly of claim 9, wherein the needle guard comprises a cap, an arm, a proximal wall, a distal wall, and a curved elbow, and wherein the curve elbow contacts the catheter hub.

14. The catheter assembly of claim 9, further comprising micro-channels formed on the elastic seal.

15. The catheter assembly of claim 9, wherein the needle further comprises a change in profile located proximally of the needle tip.

16. A method for manufacturing a catheter assembly comprising:
   forming a catheter hub with a catheter tube having a tube end, said catheter hub comprising a body defining an interior cavity having an interior surface with an interior shoulder;

forming a needle hub with a needle having a needle tip, a nominal needle diameter, and a needle shaft projecting through the catheter hub and the catheter tube such that the needle tip extends distally of the tube end in a ready position;

placing an elastic seal in the interior cavity of the catheter hub and against the interior shoulder, said elastic seal comprising an outside diameter, an inside diameter, and a side surface located between the inside and outside diameters and wherein said inside diameter being sufficiently larger than the nominal needle diameter so that the needle shaft does not come in contact with the inside diameter of the elastic seal in the ready position;

placing a needle guard for covering the needle tip in a protective position in the interior cavity of the catheter hub and in contact with the elastic seal; and forming a temporary seal for limiting fluid flow through the elastic seal at a point where the needle guard contacts the elastic seal.

17. The method of claim 16, further comprising pushing the guard into the interior cavity of the catheter hub with an installation tool comprising a lengthwise channel.

18. The method of claim 16, further comprising a hydrophobic filter mounted at a distal opening of the needle guard.

19. The method of claim 16, further comprising pushing the guard so that an outside surface of the guard is sealed against the inside diameter of the elastic seal.

20. The method of claim 16, further comprising adding a coating onto a surface of the needle guard that contacts the needle shaft.

21. The method of claim 16, wherein the needle guard exerts a force on a distally sloping surface of the interior surface of the catheter hub to force the needle guard against the elastic seal.

* * * * *